(12) United States Patent
Tao

(10) Patent No.: US 9,206,225 B2
(45) Date of Patent: Dec. 8, 2015

(54) MATERIALS AND METHODS FOR ISOLATING PHOSPHOPEPTIDES

(71) Applicant: Purdue Research Foundation, West Lafayette, IN (US)

(72) Inventor: Weiguo Andy Tao, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 320 days.

(21) Appl. No.: 13/930,316

(22) Filed: Jun. 28, 2013

(65) Prior Publication Data

US 2014/0322820 A1    Oct. 30, 2014

Related U.S. Application Data

(63) Continuation of application No. 12/575,180, filed on Oct. 7, 2009, now Pat. No. 8,501,486.

(60) Provisional application No. 61/103,268, filed on Oct. 7, 2008.

(51) Int. Cl.
| | |
|---|---|
| *G01N 33/68* | (2006.01) |
| *C07K 1/14* | (2006.01) |
| *G01N 33/58* | (2006.01) |
| *C07K 1/20* | (2006.01) |
| *C07K 1/22* | (2006.01) |

(52) U.S. Cl.
CPC ... *C07K 1/14* (2013.01); *C07K 1/20* (2013.01); *C07K 1/22* (2013.01); *G01N 33/582* (2013.01); *G01N 33/68* (2013.01); *G01N 33/6839* (2013.01); *G01N 33/6842* (2013.01); *G01N 33/6848* (2013.01)

(58) Field of Classification Search
CPC ............ G01N 33/6842; G01N 33/582; G01N 33/6839; G01N 33/6848; G01N 33/68; A61K 38/00
See application file for complete search history.

(56) References Cited

PUBLICATIONS

Quantitative phosphoproteome analysis using a dendrimer conjugation chemistry and tandem mass spectrometry W. Andy Tao, Bernd Wollscheid, Robert O'Brien, Jimmy K. Eng, Xiao-jun Li, Bernd Bodenmiller, Julian D. Watts, Leroy Hood, and Ruedi Aebersold Nature Methods vol. 2 No. 8, Aug. 2005.*

(Continued)

*Primary Examiner* — Krishnan S Menon
*Assistant Examiner* — Dwan A Gerido
(74) *Attorney, Agent, or Firm* — Brown Rudnick LLP

(57) ABSTRACT

Protein phosphorylation is a major post-translational modification and it plays a pivotal role in numerous cellular functions. We present a composition that includes a soluble nanopolymer core functionalized with groups having an affinity for either metal ion or metal oxides which can be used for phosphopeptide enrichment. Exemplary compounds including PolyMAC-Zr, PolyMAC-Fe and PolyMAC-Ti demonstrate outstanding reproducibility, exceptional sensitivity, fast chelation time, and high phosphopeptide recovery from standard mixtures that include phosphorylated peptides. The composition can be used for phosphoproteome isolation from samples of medicinal, diagnostic or biological interest such as malignant breast cancer cells. Such compositions were used for the quantitative analysis of the changes in the tyrosine phosphoproteome in highly invasive breast cancer cells after induction of Syk kinase, a potent suppressor of tumor growth and metastasis. The composition and method disclosed herein offers an efficient and widely applicable tool for phosphoproteomics.

13 Claims, 13 Drawing Sheets

(56) References Cited

PUBLICATIONS

Immobilized Zirconium Ion Affinity Chromatography for Specific Enrichment of Phosphopeptides in Phosphoproteome Analysis Shun Feng, Mingliang Ye, Houjiang Zhou, Xiaogang Jiang, Xingning Jiang, Hanfa Zou, and Bolin Gong Molecular and Cellular Proteomics 6.9, 2007.*

Soluble nanopolymer based phosphoproteomics for studying protein phosphatase Minjie Guo, Jacob Galan, and W. Andy Tao Methods 42, 2007.*

Biochemical Reagents Kits Offer Scientists Good Return on Investment Holly Ahern The Scientist 1995, 9(15):Jul. 20, 1995.*

Ahern, 1995, Biochemical, Reagents Kits Offer Scientists Good Return on Investment, The Scientist 1995, 9(15):20.

Cohen, 2002, The Origins of Protein Phosphorylation, Nature Cell Biology 4:E127-E-130.

Coopman et al., 2000, The SYK Tyrosine Kinase Supresses; Malignant Growth of Human Breast Cancer Cells in Nature, Letters to Nature 406:742.

Feng et al., 2007, Immobilized Zirconium Ion Affinity Chromatography for Specific Enrichment of Phosphopeptides in Pohsphoproteome Analysis, Molecular and Cellular Proteomics 6.9:1656-1665.

Guo et al., 20007, Soluble Nanopolymer-Based Phosphoproteomios for Studying Protein Phosphatase, Methods 42:289-297.

Tao et al., 2005, Quantitative Phosphoproteome Analysis Using a Dendrimer Cinjugation Chemistry and Tandem Mass Spectrometry, Nature Methods 2(8):591-598.

Turner et al., 2000, Tyrosine Kinase SYK: Essential Functions for Immunoreceptor Signallingin, Immunology Today 21 (3):148-154.

Zhang et al., 2009, Role of the Protein Tyrosine Kinase Syk in Regulating Cell-Cell Adhesion and Motility in Breast Cancer Cells, Zhang X. et al., Mol. Cancer Res. 7(5):634-44.

* cited by examiner

| Protein Identified | Sequence | Potential role In breast cancer |
| --- | --- | --- |
| Prostaglandin E synthase 3 | EDVDLPEVDGADDDpSQDpSDDEK Seq.1 DWEDDpSDEDMSNF Seq.12 | Disruptor of transcriptional activation |
| Membrane-associated progesterone receptor 1 | GDQPAASGDpSDDDEPPPLPR EGEEPTVpYSDEEEPK GEEPSEYpTDEEDTK Seq. 2 | Activated in acute carcinomas |
| Nuclear ubiquitous casein | VVDYSFQEpSDDADEDYGR Seq. 3 | DNA damage-related |
| Melanoma antigen D4 | ApT*WRAGVSSGTNGGASTS Seq. 4 | Highly expressed in tumors |
| cAMP-dependant protein kinase I | EDEIpSPPPNPVVK Seq. 5 | Involved in cell survival |
| Protein kinase C (iota) | TNEPVQLpT*PDDDDIVR Seq. 6 | Involved in apoptosis, signaling, microtubules dynamics |
| eIF-2B | DAEEDEEDGEFpS*DDpS*GADQEK Seq. 7 | Translation initiator |
| Plasminogen activator inhibitor 1 | DELTDLDQpSNVpT*EETPETENK Seq. 8 | Protease inhibitor |
| Serine/threonine kinase OSR1 | TEDGGWEWpS*DDEFDEESEEGK Seq. 9 | Regulator of actin cytoskeleton |
| Nuclear inhibitor of protein phosphatase 1 | PQpT*LPpS*AVKGDEKM Seq. 10 | Oncogene involved in uncontrolled growth in cancer |
| FACT complex subunit SSRP1 | EGMNFSYDEYADpSDEQHDAYLER Seq. 11 | Involved in transcription |

Figure 12

SEQUENCE LISTING

<160> NUMBER OF SEQ ID NOS: 12

<210> SEQ ID NO 1
<211> LENGTH: 13
<212> TYPE: PRT
<213> ORGANISM: Homo sapiens

<400> SEQUENCE: 1

Asp Trp Glu Asp Asp Ser Asp Glu Asp Met Ser Asn Phe
1               5                   10

<210> SEQ ID NO 2
<211> LENGTH: 49
<212> TYPE: PRT
<213> ORGANISM: Homo sapiens

<400> SEQUENCE: 2

Gly Asp Gln Pro Ala Ala Ser Gly Asp Ser Asp Asp Glu Pro Pro
1               5                   10                  15

Pro Leu Pro Arg Glu Gly Glu Glu Pro Thr Val Tyr Ser Asp Glu Glu
                20                  25                  30

Glu Pro Lys Gly Glu Glu Pro Ser Glu Tyr Thr Asp Glu Glu Asp Thr
            35                  40                  45

Lys

<210> SEQ ID NO 3
<211> LENGTH: 18
<212> TYPE: PRT
<213> ORGANISM: Homo sapiens

<400> SEQUENCE: 3

Val Val Asp Tyr Ser Phe Gln Glu Ser Asp Asp Ala Asp Glu Asp Tyr
1               5                   10                  15

Gly Arg

<210> SEQ ID NO 4
<211> LENGTH: 18
<212> TYPE: PRT
<213> ORGANISM: Homo sapiens

<400> SEQUENCE: 4

Ala Thr Trp Arg Ala Gly Val Ser Ser Gly Thr Asn Gly Gly Ala Ser
1               5                   10                  15

Thr Ser

<210> SEQ ID NO 5
<211> LENGTH: 13
<212> TYPE: PRT
<213> ORGANISM: Homo sapiens

<400> SEQUENCE: 5

Glu Asp Glu Ile Ser Pro Pro Asn Pro Val Val Lys
1               5                   10

<210> SEQ ID NO 6
<211> LENGTH: 16
<212> TYPE: PRT
<213> ORGANISM: Homo sapiens

<400> SEQUENCE: 6

Thr Asn Glu Pro Val Gln Leu Thr Pro Asp Asp Asp Ile Val Arg
1               5                   10                  15

```
<210> SEQ ID NO 7
<211> LENGTH: 21
<212> TYPE: PRT
<213> ORGANISM: Homo sapiens

<400> SEQUENCE: 7

Asp Ala Glu Glu Asp Glu Glu Asp Gly Glu Phe Ser Asp Asp Ser Gly
1               5                   10                  15

Ala Asp Gln Glu Lys
            20

<210> SEQ ID NO 8
<211> LENGTH: 21
<212> TYPE: PRT
<213> ORGANISM: Homo sapiens

<400> SEQUENCE: 8

Asp Glu Leu Thr Asp Leu Asp Gln Ser Asn Val Thr Glu Glu Thr Pro
1               5                   10                  15

Glu Thr Glu Asn Lys
            20

<210> SEQ ID NO 9
<211> LENGTH: 21
<212> TYPE: PRT
<213> ORGANISM: Homo sapiens

<400> SEQUENCE: 9

Thr Glu Asp Gly Gly Trp Glu Trp Ser Asp Asp Glu Phe Asp Glu Glu
1               5                   10                  15

Ser Glu Glu Gly Lys
            20

<210> SEQ ID NO 10
<211> LENGTH: 15
<212> TYPE: PRT
<213> ORGANISM: Homo sapiens

<400> SEQUENCE: 10

Pro Gln Thr Leu Pro Ser Ala Val Lys Gly Asp Glu Lys Met Lys
1               5                   10                  15

<210> SEQ ID NO 11
<211> LENGTH: 23
<212> TYPE: PRT
<213> ORGANISM: Homo sapiens

<400> SEQUENCE: 11

Glu Gly Met Asn Phe Ser Tyr Asp Glu Tyr Ala Asp Ser Asp Glu Gln
1               5                   10                  15

His Asp Ala Tyr Leu Glu Arg
            20

<210> SEQ ID NO 12
<211> LENGTH: 22
<212> TYPE: PRT
<213> ORGANISM: Homo sapiens

<400> SEQUENCE: 12

Glu Asp Val Asp Leu Pro Glu Val Asp Gly Ala Asp Asp Asp Ser Gln
1               5                   10                  15

Asp Ser Asp Asp Glu Lys
            20
```

MATERIALS AND METHODS FOR ISOLATING PHOSPHOPEPTIDES

PRIORITY CLAIM

This application is a continuation of U.S. nonprovisional patent application Ser. No. 12/575,180 filed on Oct. 7, 2009, which claims the benefit of U.S. provisional patent application No. 61/103,268 filed on Oct. 7, 2008, each of which is incorporated herein by reference in its entirety.

STATEMENT OF GOVERNMENT RIGHTS

This invention was made with support from the government under grant number CHE-0645020 awarded by the National Science Foundation the government has certain rights in the invention.

FIELD OF THE INVENTION

This disclosure is directed to materials and methods of purifying phosphorylated peptides in a heterogenous environment, and their use, for example, in identifying differentially phosphorylated peptides.

BACKGROUND

Reversible protein phosphorylation has been shown to be among the most widespread of all known post-translational modifications; for example, it is estimated that about 30% of all human proteins are phosphorylated at one time or another. This post-translational modification plays an important role in the regulation of many cellular functions, including growth, differentiation, and signaling. Changes in phosphorylation dynamics within the cell has been linked to the onset and development of numerous diseases, for example some forms of cancer. For additional information about the role of protein phosphorylation please see publication such as: "*The Origins of Protein Phosphorylation*," Philip Cohen, *Nature Cell Biology* 4, E127-E-130 (2002); "*Protein Phosphorylation: A Practical Approach*", Oxford University Press, USA, Dec. 15, (1999); and "*Protein Phosphorylation Methods in Enzymology*," Academic Press, May 1, (1998).

Accordingly, in order to understand normal development and metabolism, as well as diseases and various disorders it is crucial to develop a better understanding of protein phosphorylation. Given its central role in human, animal and event plant health research related to protein phosphorylation is of great interest to the scientific community, creating a need for new materials and methods to track phosphorylation, some aspects of the invention described herein address this need.

SUMMARY

Some embodiment include a composition suitable for the recovery of phosphopeptides from a heterogeneous or homogenous mixture, comprising: a synthetic soluble nanopolymer; at least one phosphonate group; and at least one metal or metal oxide, the metal or metal oxide having an affinity for at least one phosphorylated residue in a phosphopeptide, wherein the at least one phosphonate group is attached to said soluble nanopolymer and the at least one phosphonate group chelates with the at least one metal or metal oxide.

In some embodiments the composition further includes: at least one support structure; and at least one reactive group, wherein the reactive group is attached to the synthetic soluble nanoparticle and the reactive group interacts with the support structure. In some embodiments the metal in the composition is selected from the group consisting of: iron, copper, gallium, cobalt, nickel, calcium, zinc, cadmium, silver, palladium, platinum, and ruthenium. In still other embodiments the metal is selected from the group consisting of: titanium, zirconium, aluminum, vanadium, lead, manganese and tin. And in some embodiments the composition comprises a metal oxide that is selected from the group consisting of: titanium oxide, zirconium oxide and tin oxide, aluminum oxide, vanadium oxide, lead oxide and manganese oxide.

In some embodiments there is at least one reactive group attached to the synthetic nanopolymer the reactive group may be part of a bi-conjugation coupling pair, selected from group consisting of: hydrazine-aldehyde, azide-alkyne, thiol-iodoaceto, thiol-maleimide and NHS-amine. In some embodiments the synthetic soluble nanopolymer is selected from the group consisting of: polyamidoamine dendrimers, polyallyric amines, polylysine, polyarginine, polyethylene glycol derivatives, and dextran derivatives. And in some embodiment the composition includes as support structure that may include an aldehyde on the surface of the structure that react with a reactive group on the surface of the soluble nanopolymer.

In some embodiments the composition the support structure in the composition according is a bead.

While in some embodiments the support structure is selected from the group consisting of: columns, films and membranes.

Still another embodiment is a method of enriching for, extracting, purifying or identifying at least one phosphopeptide in a heterogeneous or homogenous mixture, comprising steps of: providing a composition that interacts with a composition for the recovery of phosphopeptides, said composition including: a synthetic nanopolymer; a metal or a metal oxide, wherein said metal or metal oxide has an affinity for at least one phosphorylated residue in a phosphopeptide; a first functional group that chelates with the metal or the metal oxide; a solid support; and a second functional group that conjugates to the solid support, wherein the first functional group and the second functional groups are attached to the soluble synthetic nanopolymer; obtaining a sample wherein the sample includes at least one phosphopeptide; and contacting the sample with the composition.

In some embodiments the method of enriching, extracting, purifying or identifying a phosphopeptide in a sample further includes the steps of: recovering at least a portion of said composition that was in contact with the sample; eluting the phosphopeptide from the portion of the composition and saving at least a portion of the eluent; and analyzing the eluent for the presence of at least one phosphopeptide. In some embodiments the method further includes the steps of extracting at least one phosphopeptide from a sample; and identifying at least one phosphopeptide or the lack thereof which from the sample. In some embodiments the eluent is analyzed by mass spectrometry. While in still other embodiments the eluent is analyzed by contacting at least a portion of the eluent with at least one antibody that is known to bind to at least one phosphopeptide.

In some embodiment the compositions used in the method for enriching, extracting, purifying or identifying phosphopeptides includes a soluble synthetic nanopolymer selected from the group consisting of: polyamidoamine dendrimers, polyallyric amines, polylysine, polyarginine, polyethylene glycol derivatives, and dextran derivatives. In some embodiments the composition includes a metal is selected from the group consisting of: iron, copper, gallium, cobalt, nickel, calcium, zinc, cadmium, silver, palladium, platinum, and ruthenium. In still other embodiments the metal in the composition is selected from the group consisting of: titanium, zirconium, aluminum, vanadium, lead, manganese and tin. And in some embodiments the composition includes a metal oxide is selected from the group consisting of: titanium oxide, zirconium oxide and tin oxide, aluminum oxide, vanadium oxide, lead oxide and manganese oxide.

In some embodiments the composition used to extract a phosphopeptide from a mixture or enrich a sample in the same includes a second functional group attached to the synthetic nanoparticle that is part of a bi-conjugation coupling pair, selected from group consisting of: hydrazine-aldehyde, azide-alkyne, thiol-iodoaceto, thiol-maleimide and NHS-amine. And in some embodiments the composition includes a support structure that has an aldehyde on the surface of the support structure that interacts with the synthetic nanopolymer. In some embodiments the support structure is a bead, while in other embodiments the support structure is selected from the group consisting of: columns, films and membranes.

Some embodiments include a kit suitable for identifying phosphorylated peptides or the lack thereof, in a given sample in which the kit includes at least one composition comprising: a synthetic nanopolymer, at least one phosphonate group; and at least one metal or metal oxide, the metal or metal oxide having an affinity for at least one phosphorylated residue in a phosphopeptide, wherein the at least one phosphonate group is attached to said synthetic nanopolymer and the at least one phosphonate group chelates with the at least one metal or metal oxide. In some kits the synthetic nanopolymer is selected from the group consisting of: polyamidoamine dendrimers, polyallyric amines, polylysine, polyarginine, polyethylene glycol derivatives, and dextran derivatives. In some embodiments the synthetic nanopolymer is a soluble synthetic nanopolymer.

Some embodiments such as a polymer-based metal ion or metal oxide capturing (PolyMAC) are suitable for the recovery of phosphopeptides from mixtures. The composition, may for example, comprise a soluble synthetic nanopolymer, that includes a first functional group chelating with a metal that exhibits affinity for at least one phosphorylated residue in a phosphopeptide. In some embodiments the composition has a phosphonate group as the first function group chelating with the metal. In some embodiments, the metal may be selected from the group of metals including Ti, Zr, and Sn and the like, this especially useful if the polymer is used to isolate singly-phosphorylated peptides. In still other embodiments, the metal may be selected from the group including Fe and Ga this is especially useful if the polymer is used to isolate multi-phosphorylated peptides. In additional embodiments, the metal may be selected from the group of metal that includes Co, Ni and the like this is especially useful if the polymer is used to isolate His-tagged proteins. The polymer may also include a second function group that conjugates to a solid support. In one embodiment, the second functional group is hydroxylamine, and the solid support is comprised of oxidized aldehyde beads. The nanopolymer may be selected from the group consisting of polyamidoamine dendrimers, polyallyric amines, polylysines, polyarganines, derivatives of PEG and the like.

Another group of embodiments include methods of isolating phosphopeptides. In some embodiments the methods comprise the steps of: (a) providing a comporoung comprising a soluble synthetic nanopolymer, wherein the nanopolymer includes a first functional group that chelates with at least one metal that exhibits affinity for at least one phosphorylated residue in a phosphopeptide, and a second functional group that conjugates to a solid support; (b) contacting the nanopolymer with at least one phosphopeptide in the presence of the at least one metal. In some embodiments the reagent further includes a solid support, wherein the solid support conjugates with the second functional group in the nanopolymer. In some embodiments the first functional group chelating with the metal is a phosphonate group. And the metal may be at least one metal selected from the group of metals including Ti, Zr, Sn and the like this is especially useful if the polymer is used, for example. to isolate singly-phosphorylated peptides; or from another group including Fe and Ga this is especially useful if the polymer is used, for example, to isolate multi-phosphorylated peptides; or from yet another group including Co and Ni this is especially useful if the polymer is used, for example, to isolate His-tagged proteins. In some embodiments the second functional group that conjugates to the solid support may be hydroxylamine, the solid support may be comprised of beads that are attached to an aldehyde, and the synthetic nanopolymer may be a polyamidoamine dendrimer, a polyallyric amine, a polylysine, a polyarginine, a derivative of PEG, a derivative of dextran or the like.

Yet another set of embodiments includes methods for identifying phosphorylated peptides or the lack thereof which may be associated with certain diseases, for example, cancer cells. The method comprises steps of: (a) providing a composition comprising a soluble synthetic nanopolymer, wherein the nanopolymer includes a first functional group that chelates with a metal that exhibits affinity for at least one phosphorylated residue in a phosphopeptide, and a second functional group that conjugates to a solid support; (b) contacting the nanopolymer to either a diseased cell lysate or a normal cell in the presence of the metal, and the solid support; (c) extracting at least one phosphopeptides from each lysate; and (d) identifying any phosphopeptide or the lack thereof which is associated with the disease. In one embodiment the first function group chelating with the metal is a phosphonate group. The metal may be any metal selected from a group comprising Ti, Zr, and Sn if the polymer is used to isolate singly-phosphorylated peptides; or from the group comprising Fe and Ga if the polymer is used to isolate multi-phosphorylated peptides; or from the group comprising Co and Ni if the polymer is used to isolate His-tagged proteins. In one embodiment, the second functional group is hydroxylamine, and the solid support is comprised of aldehyde beads. The nanopolymer may be polyamidoamine, polyallic amines, or polylysines.

Still another embodiment is a kit for identifying phosphorylated peptides or the lack thereof that are associated with certain conditions, including for example the presence of cells in a given sample. The kit includes a compound comprising a soluble synthetic nanopolymer, which includes a first functional group that chelates with a metal that exhibits affinity for at least one phosphorylated residue in a phosphopeptide; a second functional group that binds to a solid support; and a solid support. The nanopolymer may be selected from group consisting of polyamidoamine dendrimers, polyallyric amines, polylysines, polyarganines, derivatives of dextran, derivatives of PEG and the like. The synthetic nanopolymer may be soluble.

These and other features, aspects and advantages of the disclosure will become better understood with reference to the following drawings, description and claims.

BRIEF DESCRIPTION OF THE FIGURES

FIG. 12. Selected phosphopeptides present in Syk-induced samples, "p" adjacent to a residue indicates that the residue may be phosphorylated.

DESCRIPTION

Figure 1:
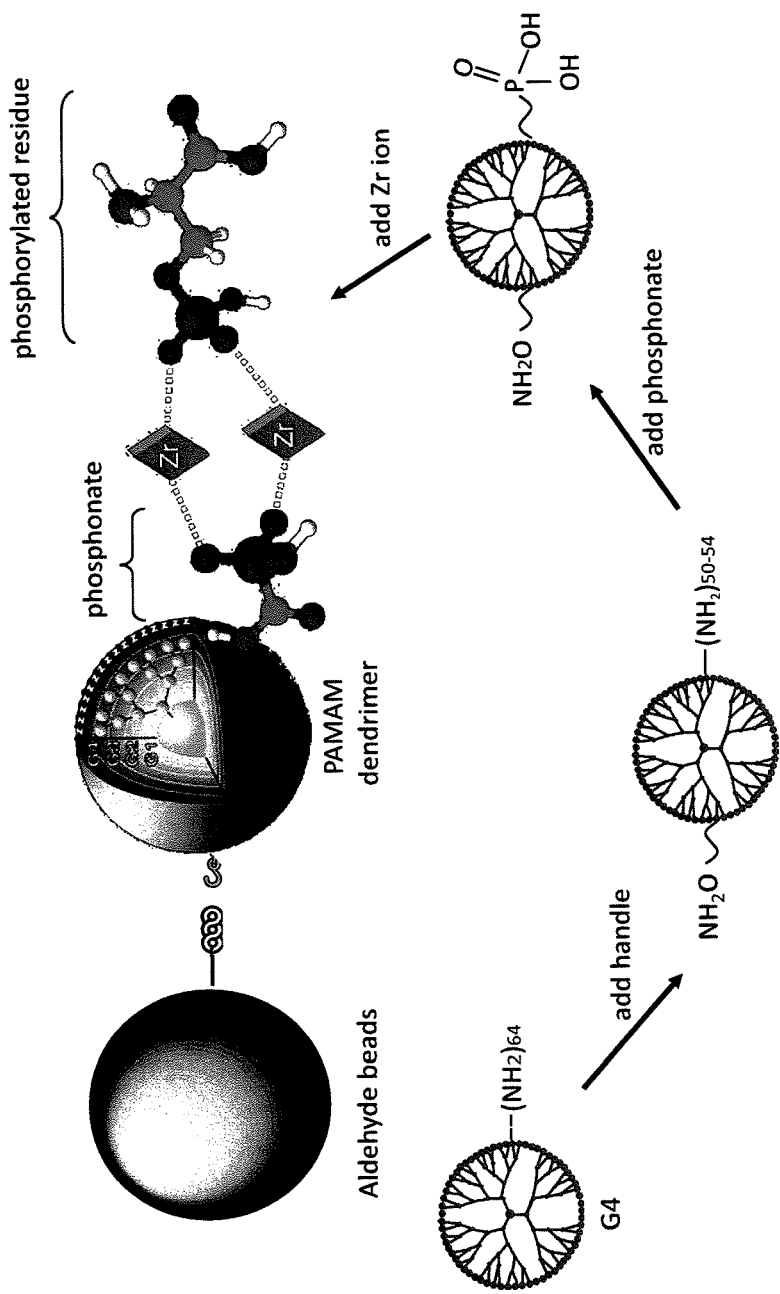
FIG. 1. A diagram illustrated one exemplary synthesis of novel soluble phospho-enrichment reagent.

While the concept of the present disclosure are illustrated and described in detail in the drawings and the description herein, such an illustration and description are to be considered as exemplary and not restrictive in character, it being understood that only the illustrative embodiments are shown and described and that all changes and modifications that come within the spirit of the disclosure are desired to be protected.

Protein phosphorylation and de-phosphorylation play a fundamental role in the both normal cell development and in a myriad of diseases and disorders. For example, the phosphorylation state of various proteins plays a central role in process such as apoptosis, aggressive growth, abnormal proliferation, the invasive growth of tumor cells, metastasis of cancer cells as well as normal cell growth, statis and death.

Accordingly, there is a glaring need to identify proteins that are phosphorylated in both normal and abnormal cells as well as tracking their phosphorylation states in various stages of cell growth, development and pathology.

To that end, numerous methods have been adapted for analyzing phosphorylation states one of the most commonly used methods includes labeling the proteins with $^{32}P$. Despite its sensitivity and robustness, this technique is not suitable for global phosphoproteomic studies and biomarker discovery. Recently, mass spectrometry has emerges as the method of choice for studying in phosphorylation and the like, this advance in the art has contributed greatly to making discovery-based phosphoproteomic analysis a reality. Unfortunately, phosphorylated proteins often exist in substoichiometric ratios when compared to unmodified proteins, making it difficult to identify phosphorylated polypeptide, in particular it is difficult to use this technique to identify the exact site of polypeptide phosphorylation. In order to overcome this limitation, several phosphopeptide enrichment techniques have been developed, which enable researcher to more confidently identify phosphorylated polypeptides. Major methods that have been developed include, for example, the following: a method that includes antibody affinity-based binding, a method that involves the chemical derivatization of phospho-sites, and a method that uses a metal ion affinity-based assay.

The antibody affinity-based methods have been widely used for the selective isolation of phosphopeptides, unfortunately the high specificity and low efficiency of this technique has made it less desirable for specific uses such as screening for unknown phosphorylated proteins. Currently, the technique is most widely used only for the identification of phosphorylated proteins that interact with phosphotyrosine-directed antibodies.

The chemical modification approach has also been used frequently perhaps the most notable version of this method tracks the β-elimination of phosphates from phosphorylated serine/threonine sites and a subsequent Michael addition of a label to the site. The usefulness of this technique lies in the chemical substitution of the MS-labile phosphate group, allowing for a more confident identification of the modified residues. Additionally, attaching certain labeling groups to the polypeptide during the Michael addition step provides an opportunity for the affinity purification of the labeled polypeptide. Nonetheless, this method suffers from a number of drawbacks, including poor reproducibility and side reactions, making identification more challenging.

One of the most frequently utilized methods for the isolation of phosphopeptide is IMAC (immobilized metal affinity chromatography). The approach is based on the selective affinity of a metal ion for the phosphate group these methods usually use metals such as Fe (III) and Ga (III). However, this method suffers from poor selectivity, perhaps due to some affinity of Fe+3 and Ga+3 for acidic residues, its low specificity makes it a less attractive method than it would be otherwise. In order to overcome this pitfall, some variations of the technique include modifying acidic residues by methyl esterification before running the assay this approach has used with some success decrease nonspecific binding thereby increasing the utility of the method. Unfortunately, this modification step may be problematic due to often incomplete esterification and side reaction products that complicate the mass spectrometry analysis of the phosphorylated polypeptide.

A strategy for isolating phosphorylated polypeptides uses an oxide version of a metal. Especially successful metal oxides put to this use include $TiO_2$, $ZrO_2$ and $Al(OH)_3$ which may be used in conjunction with beads, chromatography columns and the like for the isolation of phosphopeptides. Certain metal dioxides, for example, $TiO_2$ and $ZrO_2$, have demonstrated an exceptionally high selectivity for and strong affinity for the chelation of phosphorylated residues, providing an advance in the field of phosphopeptide isolation. Despite the many advantages of titania- and zirconia-functionalized beads, there are some negative aspects of this approach including, for example, including slow reaction kinetics, modest phosphopeptide recovery, and problems with reproducibility. Potentially, at least some of these problems may be due to heterogeneous reaction conditions caused by the use of solid-phase beads and nanoparticles. Heterogeneous reaction conditions may lead to an unequal distribution of the reactive groups, reduced access to functional groups, nonlinear kinetic behavior, and solvation problems. Accordingly, there is still room for improvement even when using metal oxides in conjunction with beads to isolate phosphorylated polypeptides.

Some embodiments of the instant invention seek to address some of these limitation by introducing materials and methods for phosphopeptide enrichment that include, for example, PolyMAC-Zr (a polymer-based metal affinity capture material that includes zirconia). Compounds such as PolyMAC-Zr and the like unexpectedly overcome the problems surrounding heterogeneous reaction conditions found with simple metal oxide/bead based systems. Reagents such as PolyMAC-Zr include a soluble polyamidoamine synthetic nanopolymer (e.g. a dendrimer) that includes a hyper-branched surface which can be functionalized with various chemical groups. In addition to increased solubility, the advantages of using dendrimers include their high structural and chemical homogeneity, compact spherical shape, and readily controllable surface functionalities. Many of these compounds also possess a unique ability to cross cell membranes, and have been widely used to deliver vaccines, drugs, and genomic materials into cells. Accordingly, dendrimers can be functionalized with materials such as zirconia to create materials that are well suited for the robust and efficient isolation of phosphopeptide. Such reagents have demonstrated reproducibly high selectivity, favorable kinetics and excellent levels of phosphopeptide recovery. As discussed below, in one exemplary application, some of this material was used to analyze a sample for the presence of phosphopeptides that are thought to be created as a result of Syk kinase-induced phosphorylation. This is of special interest because the activity of Syk-kinase is different in highly invasive breast cancer cells than it is in non-cancerous breast cells.

Some embodiment include a composition, or method of using the same, that includes, but are not limited to different synthetic nanopolymers such as PAMAM polyaminoamine dendrimer, polyallyricamine, polylysine, polyarginine, PEG (polyehtylene glycol) derivatives, dextran derivatives, and the like.

Some embodiments include at least one metal or metal oxide that is attached to the synthetic nanopolymer and that interacts with at least one phosphopeptide, phosphoprotein or phospho-polypeptide including, but are not limited to, iron, gallium, copper, cobalt, nickel, cadmium, ruthenium, mercury, gadolinium, aluminum, zinc and the like.

Some embodiment include at least one metal oxide that is attached to the dendrimer and that interacts with at least one phosphopeptide, phosphoprotein or phospho-polypeptide including, but not limited to, titanium oxide, zirconium oxide, vanadium oxide, tin oxide, lead oxide and the like.

In some embodiments the dendrimers may be attached to other groups such as support structures including, but not limited to, beads, membranes, columns, using various chemically active moieties, for example bi-conjugation pairs such as hydrazine-aldehyde, azide-alkyne, thiol-iodoaceto, thiol-maleimide, NHS N-hydroxysulfosuccinimide)-amine and the like.

Spleen tyrosine kinase (Syk) is a 72 kDa signaling protein involved primarily in B cell antigen receptor signaling. The expression of Syk is lower in malignant breast cells than in normal breast cells. Moreover, when Syk was transfected into malignant breast carcinoma cells, it was found to act as a tumor suppressor, acting at least in part by, inhibiting cell motility and proliferation. Some of the most dramatic changes observed by transfecting breast cancer cells with Syk included reduced malignancy, decreased cancerous cell proliferation, and decreased metastasis. To the best of our knowledge to date there have been no published reports that identify the physiological substrates of Syk in breast cancer cells. Accordingly, elucidating Syk action in more detail will increase our understanding of breast cancer onset and progression, and should aid in the discovery and development of therapeutic targets to treat breast cancer and similar diseases.

Using PolyMAC-Ti and PolyMAC-Zr we quantitatively analyzed the changes in invasive breast cancer cell phosphoproteome before and after the induction of Syk kinase expression. As discussed further below proteins from two sets of malignant carcinoma cells (−Syk or +Syk) were digested, isotopically labeled and phosphopeptides isolated using PolyMAC-Zr, the samples were analyzed using two-dimensional microcapillary LC-tandem mass spectrometry for identification and relative quantification of phosphorylated proteins in the samples.

Experimental Methods and Results

Referring now to FIG. 1, a diagram illustrating some of the component and steps in the process of synthesizing a composing according to some embodiments of the invention. Briefly, a support structure, such a bead includes surface groups, such as aldehydes, that interact with at least one reactive group (a hydrazine) comprising a dendrimer such as PAMAM dendrimer. A second group on the surface of PAMAM dendrimer includes a functional group such as phosphonate which can be formed by the reaction of a carboxyethyl-phosphoric acid with amine groups of the dendrimer to form a phosphonate group that chelates either or both metal ions and metal oxides.

1. An Exemplary Synthesis of PolyMAC-Ti

One protocol suitable for the synthesis of compounds such as PolyMAC-Ti is as follows. Dry 200 µl of PAMAM (polyamidoamine) dendrimer generation 4 solution (provided as 10% (wt/vol) in methanol, such material available from Sigma-Aldrich is placed in a microfuge tube. Bring-up resolubilize dried dendrimer in 2 ml of anhydrous DMSO (dimethyl sulfoxide) and transfer into a 10-ml round-bottom flask with a magnetic stir bar. In a microfuge tube, add 5.5 mg of Boc-amino-oxyacetic acid, 10 mg of HOBt (hydroxybenzotriazole) and 10 µl of DIPCI (1,3-diisopropylcarbodiimide); dissolve in 1 ml of DMSO and incubate for about 30 min at room temperature. Add the mixture into the round bottom flask containing dendrimer and stir overnight. Dialyze the solution against water for 7-8 hours using, for example, Snakeskin® pleated dialysis tubing (3,500 MWCO, 22 mm dry diameter, available from Pierce) to remove any remaining unreacted reagents (replace water periodically during dialysis). Transfer the solution into an Amicon Ultra centrifugal filter device (5 kDa MW cutoff; available from Millipore) and concentrate it to a volume of about 2 ml or less. Bring the mixture up to 2 ml with water and transfer into a clean 10-ml round-bottom flask with a stir bar. Add 1 ml of 250 mM MES (2-(N-morpholino)ethanesulfonic acid; pH 5.8) (it can be used it to wash the remaining reagent out of the Amicon filter), 16 mg of carboxyethyl-phosphoric acid and 160 mg of EDC (1-ethyl-3-(3-dimethylaminopropyl) carbodiimide hydrochloride) into the flask, and stir overnight to functionalize the dendrimer with phosphonic acid. Dialyze the solution against water for 5-6 hours to remove any unreacted reagents (replace water periodically during dialysis). Concentrate again using Amicon filter tubes to the final volume of 1.5 ml. At this point, the mixture should be stored at −20° C. and the remaining synthesis steps can be done three times to using 500 µl of the mixture at one time (will produce three batches of reagent). Mix 500 µl of the above solution and 500 µl of 100 mM zirconium oxychloride ($TiOCl_2$) and incubate for 1 hour with agitation at room temperature to chelate zirconia with phosphonic acid groups on the dendrimer. Dialyze the solution overnight to remove any unbound zirconia (replace dialysis solution periodically during dialysis). Remove from dialysis and dry the solution in a glass tube under vacuum using SpeedVac concentrator (Savant). Dissolve the reagent in 100 µl of water and add 400 µl of 100% TFA (trifluoroacetic acid), incubate for 1 hour with agitation at room temperature to remove the Boc protecting group. Dry the sample and resolubilize in 750 µl of DMSO. Add 250 µl of the 4:1 mixture of 0.1% HCl in water and DMSO into the reagent solution.

2. An Exemplary Synthesis of Aldehyde-Beads.

Transfer 200 mg of controlled pore glass (CPG) beads into a Bio-Spin® disposable chromatography column (Bio-Rad). Dissolve 92 mg of Fmoc-serine-OH, 38 mg of HOBt (hydroxybenzotriazole) and 90 µl of DIPCI (1,3-diisopropylcarbodiimide) in 500 µl of DMF (dimethylformamide). Add the solution into the column containing beads and rotate the column end-over-end overnight at room temperature to couple Fmoc-serine group to the beads. Wash the beads with 4 ml of DMF. Add sequentially 250 µl of DMF, 250 µl of dichloromethane, 300 µl of pyridine, and 200 µl of acetic anhydride to the beads to block the remaining amines; rotate end-over-end for 1 hour at room temperature. Wash the beads three times with 1 ml of dichloromethane and three times with 1 ml of DMF. Add sequentially into the column 800 µl of DMF and 200 µl of piperidine to remove the Fmoc group; rotate end-over-end for 1 hour at room temperature. Wash the beads three times with 1 ml of DMF and three times with 1 ml of dichloromethane. The resulting serine beads should be dried completely using SpeedVac concentrator and stored at 4° C. Oxidation: transfer 5-7 mg of serine beads into a frit-based spin column (Bocascientific) and add 200 µl of oxidation solution (8.5 mg of sodium (meta) periodate in 200 µl of 40 mM acetic acid/sodium acetate solution) and incubate for 30 minutes with agitation in the dark at room temperature. The resulting aldehyde beads should be used on the same day.

3. Capturing Phosphopeptides Using PolyMAC-Ti

Resuspended a peptide mixture in 100 µl of the mixture of 150 mM acetic acid/100 mM sodium acetate buffer in 30% ethanol (pH 4.90). Add 10 µl of synthesized metal oxide-functionalized dendrimer solution to the peptides solution and incubate 1-2 minutes with agitation at room temperature to allow chelation of phosphopeptides to zirconia-functionalized nanopolymer. Wash the aldehyde beads (oxidized for about 30 minutes before use) with 200 µl of 0.1% TFA in the frit-based spin column by centrifuging them down at about 7,000 rpm for about 30 seconds. Add the sample reaction mixture into the spin column containing aldehyde beads and incubate for 1 hour with vigorous agitation at room temperature. Remove the sample flow-through by centrifuging the beads down at about 7,000 rpm for about 30 seconds. Wash the beads by agitating the for about 5 minutes at room temperature with: a) 100 µl of loading buffer, b) 100 µl of 1% acetic acid in 80% acetonitrile solution (twice), and c) 100 µl of water by centrifuging the beads down at about 7,000 rpm for about 30 seconds. Elute the bound phosphopeptides by incubating the beads with 100 µl of 400 mM ammonium hydroxide ($NH_4OH$) for 5 minutes (twice) with agitation at room temperature. Centrifuge down the beads at about 7,000 rpm for about 30 seconds, collect and combine the eluents. Dry the eluents under vacuum and resolubilize in 0.1% formic acid for mass spectrometry analysis.

4. Using PolyMAC to Recover Phosphopeptides

Figure 2:
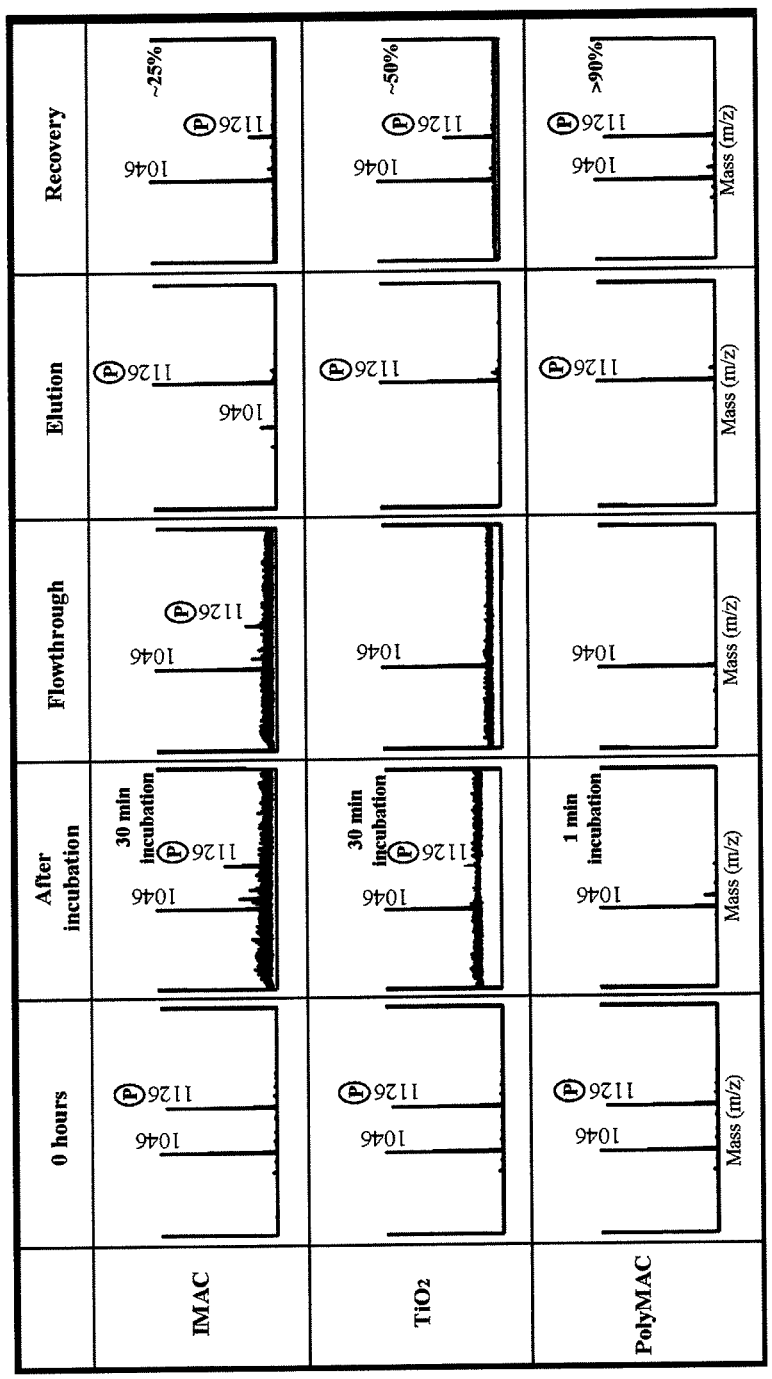
FIG. 2. A chart illustrating a kinetic comparison of different phosphor-peptide enrichment methods.

Using PolyMAC-Ti or PolyMAC-Zr based methods to recover phosphpeptides demonstrated faster recovery, higher selectively and greater yield compared to some other methods used. Referring now to FIG. 2 a kinetic comparison of enrichment methods assays were carried out on similar samples enriched from phosphopeptides using 3 different methods the samples were analyzed by mass spectrometry. Briefly, a standard peptide mixture, comprising angiotensin II peptide (m/z 1046) and its phosphorylated form (m/z 1126 Da), was incubated with IMAC, $TiO_2$, or PolyMAC-Ti, respectively. At "0 hrs", a sample was taken from each reaction mixture before the addition of the enrichment reagents. After the reagents addition, 1 µl sample of each reaction was taken out at the indicated times and analyzed by MALDI TOF/TOF mass spectrometer to compare the phosphopeptide binding kinetics of the three methods. As illustrated by the data presented in FIG. 2 PolyMAC captures phosphopeptides more efficiently than either beads functionalized with $TiO_2$ or IMAC.

Figure 3:
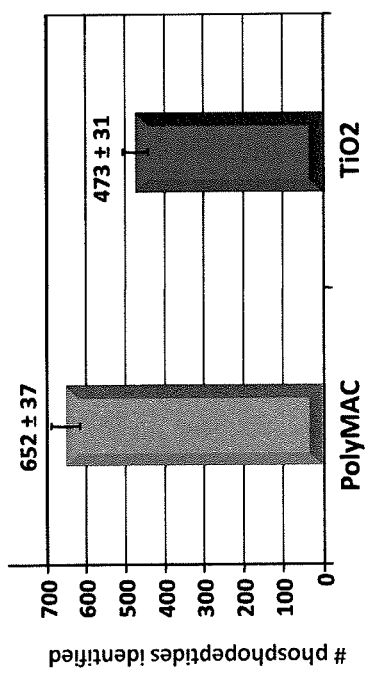
FIG. 3. A chart illustrating the relative efficiencies of PolyMAC and beads coated with $TiO_2$ nanoparticles used to enrich a sample in phosphorylated peptides.

Referring now to FIG. 3 a bar graph illustrating a comparison of selective phosphopeptide enrichment methods. After incubating a sample that includes a mixture of phosphopeptides, with either $TiO_2$ coated beads or the inventive composition including PolyMAC-Ti attached to a bead, the flow-through was collected and the beads were washed to remove nonspecific binding peptides. Next the bound peptides were eluted off the beads. All of the flow-through, wash, and elution solutions were analyzed by LTQ-Orbitrap™ in order to compare the binding selectivity of the two phosphopeptide enrichment methods. It appears that PolyMAC-Zr identified almost 200 more phosphopeptides from the same sample than did the method relying on $TiO_2$.

Figure 4:
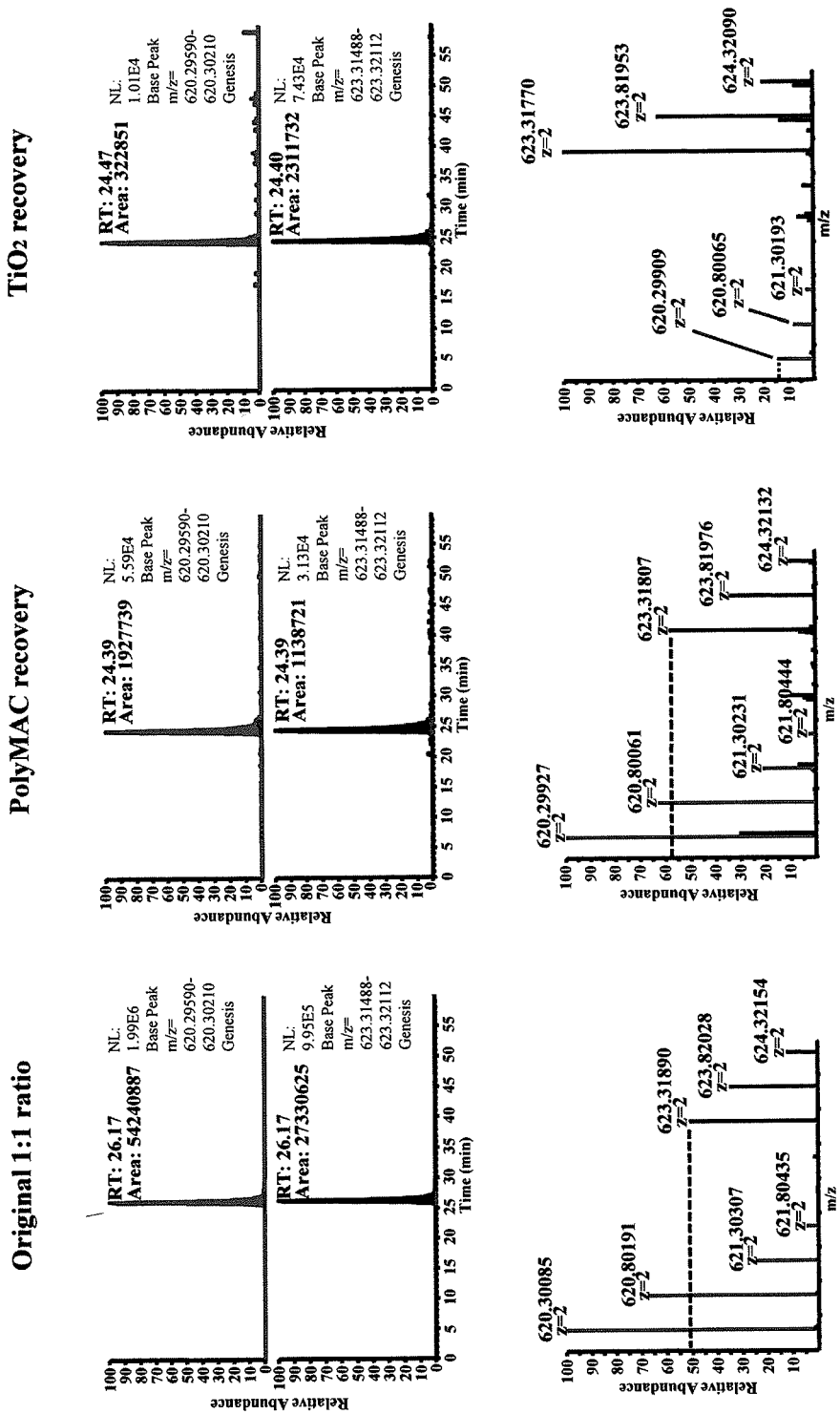
FIG. 4. Mass spectrometry data showing the relative efficiencies of 2 different methods of enriching samples in at least one phosphorylated peptide in complex samples using PolyMAC-Ti and $TiO_2$ beads.

Referring now to FIG. 4 a comparison of the yield and extent of enrichment between two different methods used to enrich in phosphopeptides in complex samples. After the elution of the bound phosphopeptides, the original amount of the unphosphorylated angiotensin II peptide—with a heavy isotope tag (m/z 623.3 for doubly charged species) was added into each elution solution to be used as an internal standard. The resulting mixture was analyzed by LTQ-Orbitrap to compare the recovery yield of phosphopeptide enrichment between the two methods tested. Recovery using the Poly-MAC—Ti based method is greater than 90% whereas recovery using the $TiO_2$ method is less than 10%.

Figure 5:
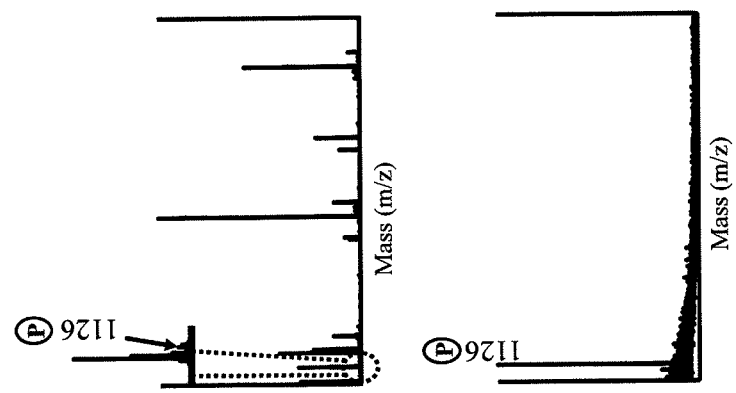
FIG. 5. Mass spectrometry data illustrating the detectable levels of a (1126 Da) phosphopeptide measured in the presence of a large amount of beta-lactoglobulin. The spectra in the upper panel were measured before the sample was treated with PolyMAC-Ti.

Referring now to FIG. 5, enrichment of phosphopeptide (m/z 1126) in a background including a large amount of beta-lactoglobulin. A, 1:100 mixture that included phosphorylated angiotensin II (MW 1126 Da) and unphosphorylated peptides made from β-lactoglobulin protein were incubated with the compound PolyMAC-Ti. After the enrichment at time "0 hrs" the elution solutions were analyzed by MALDI TOF/TOF to examine the efficiency of phosphopeptide enrichment from the high background of unphosphorylated peptides. Before enrichment (upper panel and insert therein), the phosphopeptide was almost invisible due to the presence of a much larger amount of nonphosphopeptides (100 times higher) in the sample. In contrast, after enrichment (lower panel), only the phosphopeptides were found in the elution, evidence of PolyMAC-Zr affinity for the phosphorylated peptides.

5. Another Exemplary Composition PolyMAC-Fe, is Used to Purify a Multiply-Phosphorylated Peptide.

PolyMAC-Fe is another type of exemplary reagent that is suitable for capturing phosphopeptides. The synthesis of this reagent is similar to the synthesis of PolyMAC-Ti described in the above, except that the polymer is activated with Fe (III). The protocol to use PolyMAC-Ti to enrich a sample in a phosphorylated peptide is also similar to how PolyMAC-Ti is used and may include the following steps: (1) Incubate a peptide mixture with PolyMAC-Fe for about 2 min; (2) Add aldhyde-functionalized solid phase at pH 4.5 m and incubate for about 30 min; (3) Centrifuge to remove the supernatant; (4) Wash the beads; (5) Elute the sample with base; and (6) Subject the elutant to LC-MS analysis or some other means of detecting the presence of a polypeptide in the sample.

Figure 6:
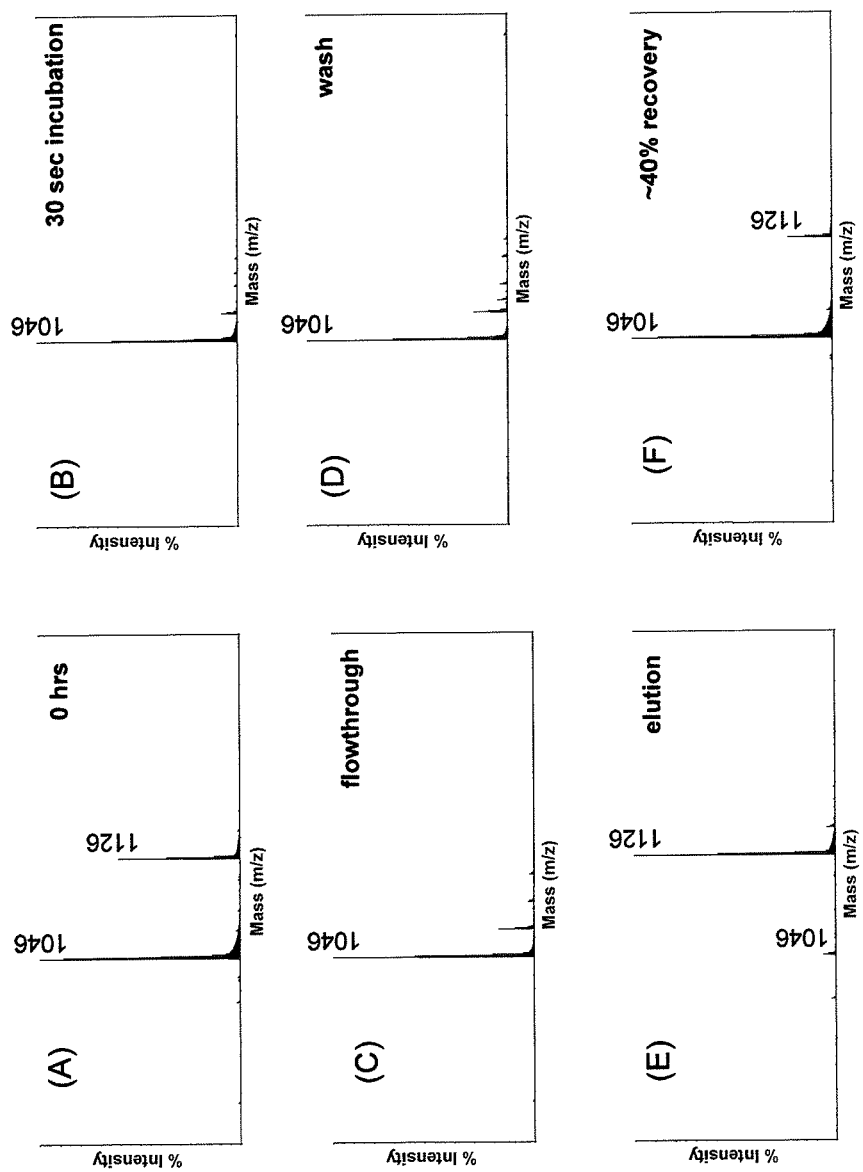
FIG. 6. Tracing showing the amount of a polypeptide in various samples drawn at various stages of an enrichment protocol using PolyMAC-Fe reagent to capture and later release a phosphopeptide.

PolyMAC-Fe preferably binds multiply-phosphorylated peptides, while PolyMAC-Ti preferably binds to singly-phosphorylated peptides. Accordingly, these 2 reagents are complementary, and the combination of the 2 of them covers the majority of phosphopeptides. Referring now to FIG. 6, the peak with a molecular weight of 1046 corresponds to angiotensin II and the ion peak with a molecular weight of 1126 corresponds to phosphorylated angiotensin. The spectra were obtained using MALDI-TOF/TOF (ABI 4800). (A) At 0 Hr.; (B) after 30 s of incubation with the capture reagent indicating the phosphopeptide (m/z 1126 was completely, or nearly completely, captured by PolyMAC-Fe); (C) The flow-through did not include a detectable level of any phosphopeptide; (D) The washing step did not cause any loss of a detectable amount of phosphopeptide; (E) Elution from the reagent yielded mainly phosphopeptide (the amount of non-phosphopeptide is estimated to be less than about 5%); (F) Data gathered by analyzing a sample that included adding the same amount of 1046 into the elution sample as was included in the standard these results indicate the yield of this recovery process is about 40%.

Figure 7:
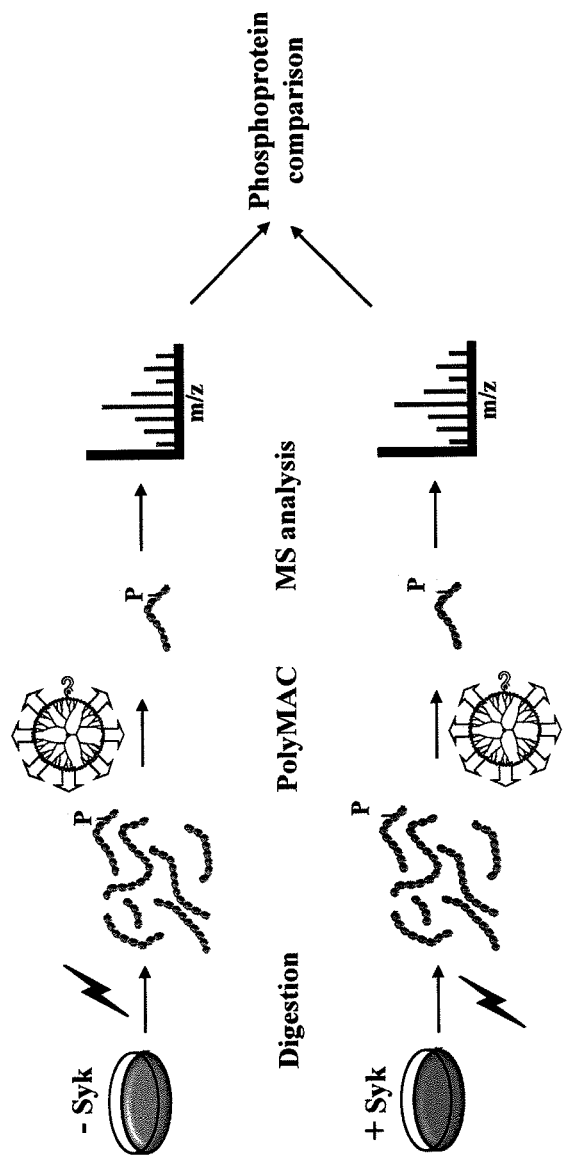
FIG. 7. Experimental flowchart illustrating the steps in analyzing breast cancer cells for phosphorylated polypeptides enriched in such sample using PolyMAC-Ti.

6. Using the Exemplary Reagent PolyMAC-Ti's in the Analysis of Breast Cancer Cell Phospho-Proteomics Referring now to FIG. 7 a flow chart highlighting some of the steps in a protocol designed to identify phosphorylated polypeptides in breast cancer cells using various methods of enriching a sample in such proteins. Briefly, breast cancer cells that did not over express the kinase Syk (upper branch) and breast cancer cells that did over-express the kinase Syk were obtained. Proteins recovered from these cells were digested to create a mixture of peptides and the mixture was contacted with PolyMAC-Ti. After washing, the bound peptides were eluted from the PolyMAC and analyzed by mass spectrometry. The patterns of polypeptides in the 2 samples were compared.

Some cancers are thought to involve abnormal patterns of phosphorylation. For example, some forms of breast cancer the single most common form of cancer diagnosed in American women are thought to involve abnormal phosphorylation states. Spleen Tyrosine Kinase (Syk) is an enzyme that has been shown to missing or at least present at abnormally low levels in some breast cancer cells. For an additional discussion of Syk activity in highly invasive breast cancer cells please see articles such as Turner, et al., in *Immunology Today*, 21:148 (2000) and Coopman et al., in *Nature* 406:742 (2000).

Figure 8:
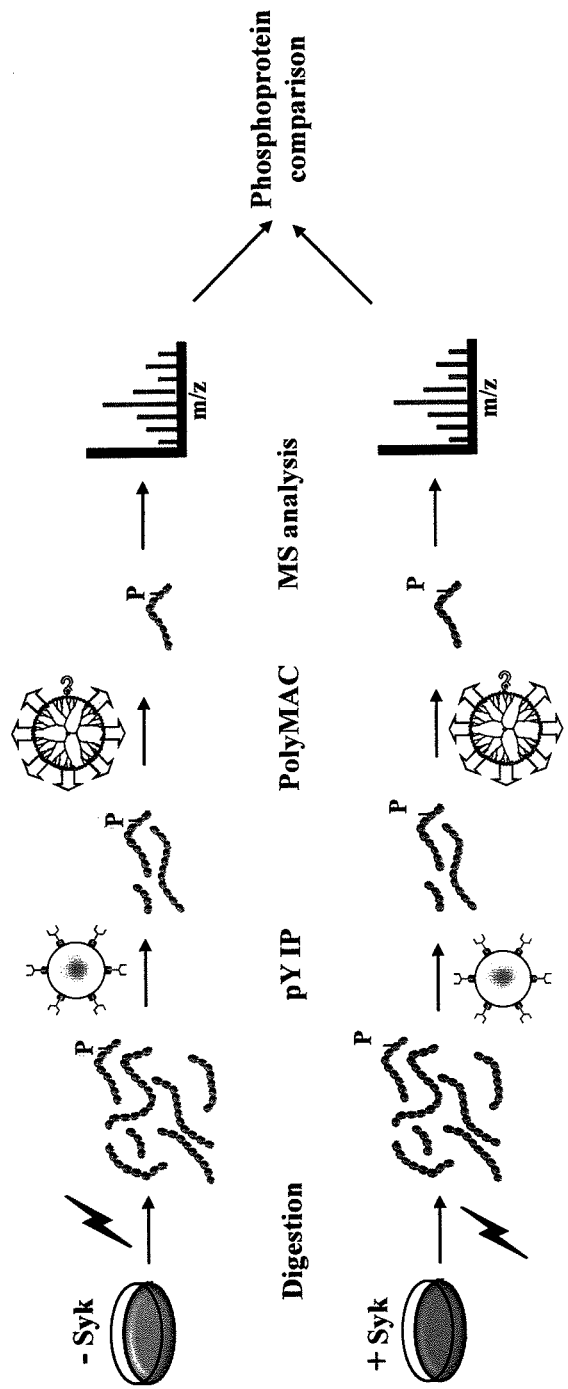
FIG. 8. Experimental flowchart illustrating the steps in analyzing breast cancer cells for phosphorylated polypeptides enriched in such sample using PolyMAC-Ti, this protocol includes the step of subjecting the samples to an anti-phosphotyrosine antibody affinity purification (pYIP) step before adding PolyMAC-Ti.

Referring now to FIG. 8 the outline of an experimental protocol for analyzing for the presence of Syk-induced changes in phospho-proteome in breast cancer cells. Briefly, 2 sets of invasive cancer MDA-MB-231 cells (Syk-negative or Syk-induced) are lysed, the proteins digested with trypsin, and the resulting peptides are first enriched for tyrosine phosphopeptides. PolyMAC-Ti is used to further isolate tyrosine phosphopeptides and LTQ Orbitrap MS/MS is used to identify and determine the relative amount of the phosphoproteins in the samples.

Figure 9:
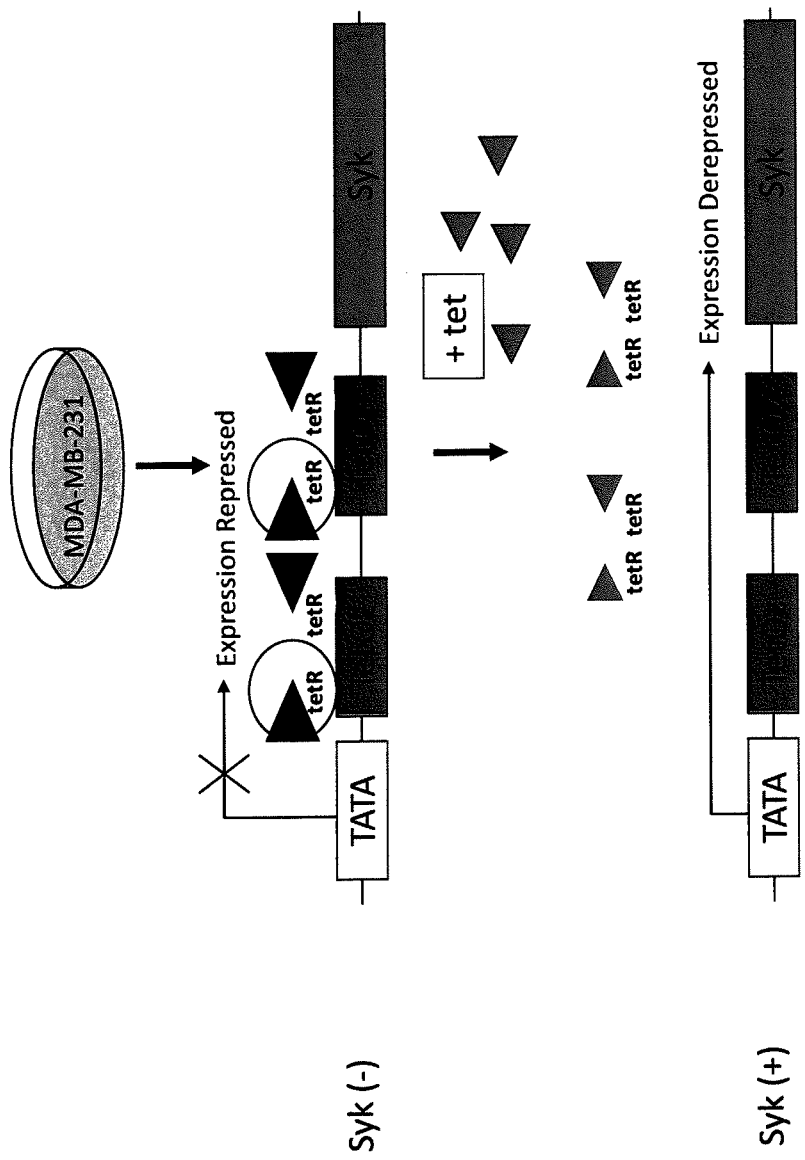
FIG. 9, Schematic diagram illustrating the components of the Tet– operator plasmids that were used to control the expression of Syk kinase in invasive breast cancer cells.
Figure 10:
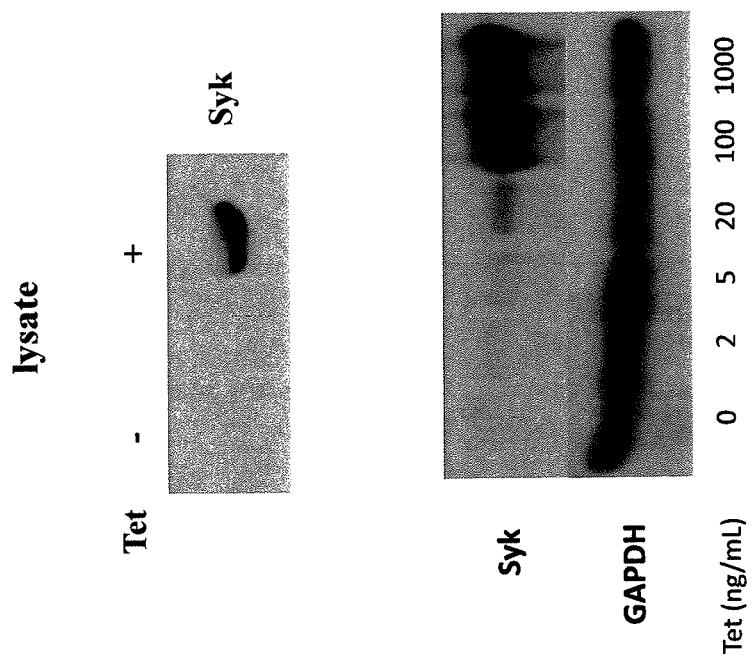
FIG. 10. Gels showing the amounts of Syk in Tet– and Tet+ MDA-MB-231 breast cancer cells (upper gel) and Syk and GAPDH (lower image) expression with different amount of Tet treatment.
Figure 11:
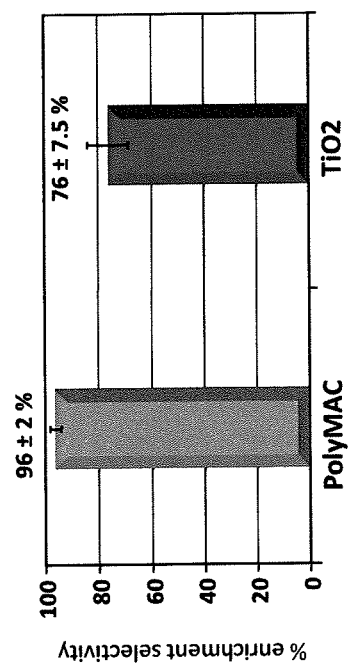
FIG. 11. Bar graph illustrating the comparison of the relative selectivity of PolyMAC-Ti and $TiO_2$ nanoparticles to engage phosphopeptides in a given sample. In the samples treated with PolyMAC-Ti about 95% of the peptides identifies from the Tet+/MDA-MB-231 cells were found to be tyrosine phosphorylated peptides. In the samples treated with $TiO_2$ about 76% of the peptides identifies from the Tet+/MDA-MB-231 cells were found to be tyrosine phosphorylated peptides.

Referring now to FIG. 9 a schematic outline of the constructs (and controls kinase Syk expression repressed) made and used to transfect MDA-MB-232 breast cancer cells. For additional details on how these constructs were created see, for example, "Role of the Protein Tyrosine Kinase Syk in Regulating Cell-Cell Adhesion and Motility in Breast Cancer Cells," Zhang X. et al., *Mol. Cancer Res.* 7(5):634-44 (2009). Referring now to FIG. 10, Western Blots of whole cell lysates run using sample collected from the human breast cancer cell line MDA-MB-232 cells transfected with inducible Syk expression systems that were either treated with Tet (+) or were not treated with Tet (−). The upper panel shows a gel showing only the region of the gel expected to include Syk. The lower gel shows portions of the gel that are expected to show Syk and GAPDH, lanes of this gel moving from left to right were loaded with the same amount of proteins recovered from cells treated with 0, 2, 5, 20, 100 and 1,000 ng mL$^{-1}$ of Tet in cell culture.

Referring now to FIG. 12, this figure shows tyrosine phosphopeptides isolated from whole cell extracts of MDA-MB-232 cells that were transfected with the Syk vectors described in the above. Samples were run in parallel to enrich them in the phosphopeptides using either PolyMAC-Ti or TiO$_2$. All of the phosphopeptides listed in FIG. 12 were identified in Syk induced samples, the boxes highlight some of more interesting proteins that were identified in the samples. All of the phosphopeptides included in FIG. 12 appear to be absent in lysates of cells made from Syk-negative cells.

Figure 13:
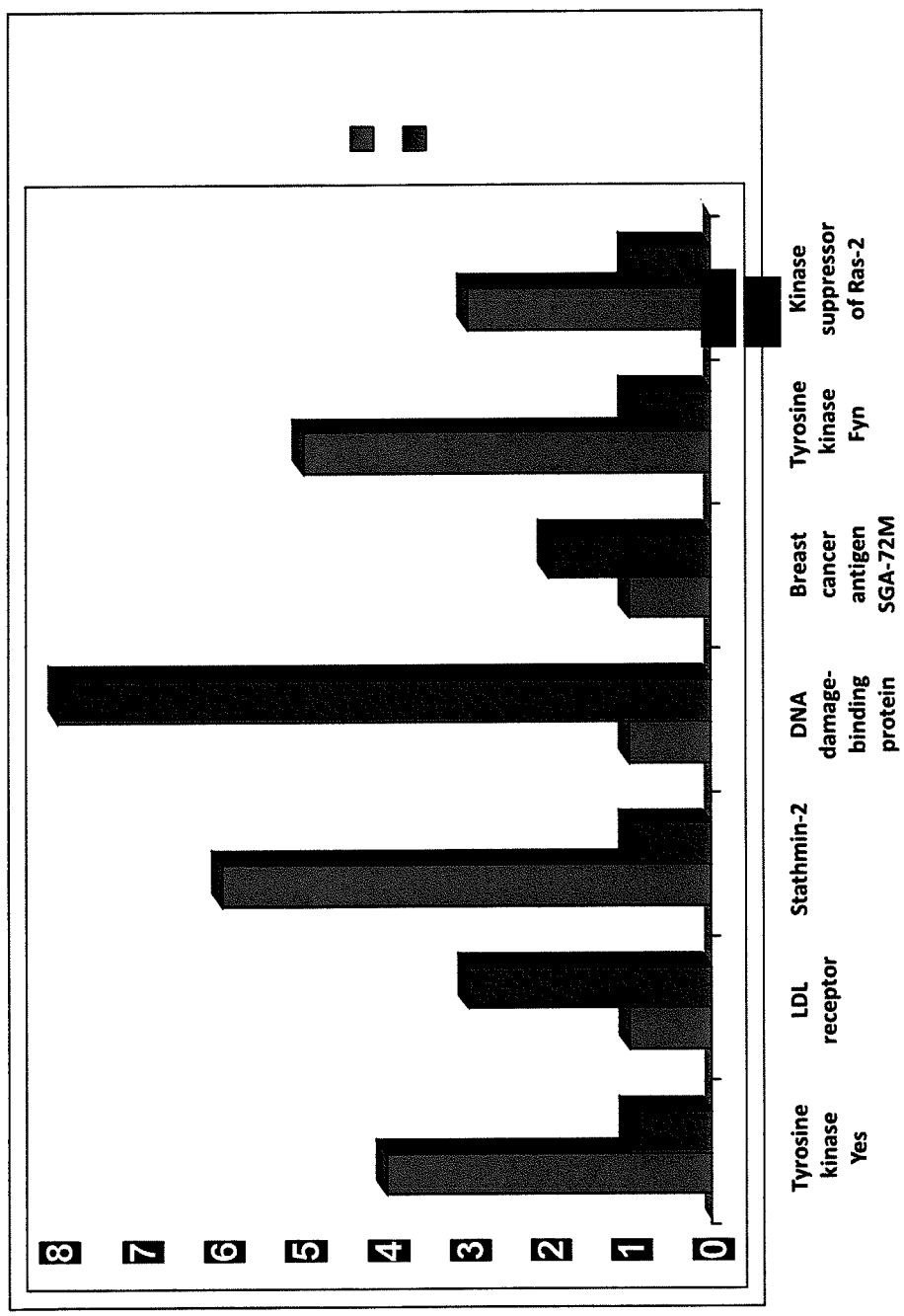
FIG. 13. A bar graph illustrating some of the tyrosine phosphorylated peptides that were identified in breast cancer cells using PolyMAC-Ti.

Referring now to FIG. 13 this figure illustrated the quantitative differences between various tyrosine kinases in Syk− and Syk+ cell lines. In each pair of bars the left most bar (blue) represents proteins in MDA-MB-232 cells transfected with Tet−; while the right most bar (red) represents proteins in MDA-MB-232 cells transfected with Tet+. Interestingly, many tyrosine containing peptides, including Tyrosine Kinase Yes, Stathmin-2 and Tyrosine kinase Fyn, Kinase suppressor of Ras-2 are less phosphorylated in the presence of the Syk than those in the absence of Syk, indicating that the sub-phosphorylation of some proteins may contribute to the malignancy of the cancer cell.

It should be understood, of course, that the foregoing relates to exemplary embodiments of the invention and that modifications may be made without departing from the spirit and scope of the invention as set forth in the following claims. It should be understood, of course, that the foregoing relates to exemplary embodiments of the invention and that modifications may be made without departing from the spirit and scope of the invention as set forth in the following claims.

I claim:

1. A method for enriching for a phosphopeptide, comprising steps of:
   providing a solid support and a composition for the recovery of phosphopeptides, said composition including: a soluble synthetic nanopolymer; a metal or a metal oxide, wherein said metal or metal oxide has an affinity for at least one phosphorylated residue in a phosphopeptide; a first functional group that chelates with the metal or the metal oxide; and a second functional group that conjugates to the solid support, wherein the first functional group and the second functional groups are attached to the soluble synthetic nanopolymer;
   obtaining a sample wherein the sample includes at least one phosphopeptide; and
   contacting the sample with the composition.

2. The method according to claim 1, wherein the soluble synthetic nanopolymer is selected from the group consisting of: polyallyric amines, polylysine, polyarginine, polyethylene glycol derivatives, and dextran derivatives polyamidoamine dendrimer.

3. The method according to claim 1, wherein the metal is selected from the group consisting of: iron, copper, gallium, cobalt, nickel, calcium, zinc, cadmium, silver, palladium, platinum, and ruthenium.

4. The method according to claim 1, wherein the metal is selected from the group consisting of: titanium, zirconium, aluminum, vanadium, lead, manganese and tin.

5. The method according to claim 1, wherein the metal oxide is selected from the group consisting of: titanium oxide, zirconium oxide and tin oxide, aluminum oxide, vanadium oxide, lead oxide and manganese oxide.

6. The method according to claim 1, wherein the second functional group is part of a bi-conjugation coupling pair, selected from group consisting of: hydrazine-aldehyde, azide-alkyne, thiol-iodoaceto, thiol-maleimide and NHS-amine.

7. The method according to claim 1, wherein the solid support includes an aldehyde on the surface of the solid support.

8. The method according to claim 1, wherein the solid support is a bead.

9. The method according to claim 1, wherein the solid support is selected from the group consisting of: columns, films and membranes extracting at least one phosphopeptides from each lysate; and identifying at least one phosphopeptide or the lack thereof which from the sample.

10. The method according claim 1, further including the steps of:
    recovering at least a portion of said composition that was in contact with the sample;
    eluting the phosphopeptide from the portion of the composition and saving at least a portion of the eluent; and
    analyzing the eluent for the presence of at least one phosphopeptide.

11. The method according claim 10, wherein the eluent is analyzed by mass spectrometry.

12. The method according claim 10, wherein the eluent is analyzed by contacting at least a portion of the eluent with at least one antibody that is known to bind to at least one phosphopeptide.

13. A kit for identifying phosphorylated peptides or the lack thereof, comprising:
    a synthetic nanopolymer, at least one phosphonate group; and
    at least one metal or metal oxide, the metal or metal oxide having an affinity for at least one phosphorylated residue in a phosphopeptide, wherein the at least one phosphonate group is attached to said polyamidoamine dendrimer and the at least one phosphonate group chelates with the at least one metal or metal oxide.

* * * * *